(12) United States Patent
Benado

(10) Patent No.: US 6,280,197 B1
(45) Date of Patent: Aug. 28, 2001

(54) METHOD AND APPARATUS FOR THE WITHDRAWAL OF DENTAL POST

(76) Inventor: Doron Benado, 61 Sderot Yerushalavin, Ramat Gan 52371 (IL)

( * ) Notice: Subject to any disclaimer, the term of this patent is extended or adjusted under 35 U.S.C. 154(b) by 0 days.

(21) Appl. No.: 09/477,382

(22) Filed: Jan. 4, 2000

(51) Int. Cl.$^7$ .................................................. A61C 3/02
(52) U.S. Cl. ........................................ 433/224; 433/165
(58) Field of Search .................................. 433/165, 224, 433/215

(56) References Cited

U.S. PATENT DOCUMENTS

| | | | |
|---|---|---|---|
| 1,123,730 | * | 1/1915 | Greenfield . |
| 1,216,683 | * | 2/1917 | Greenfield . |
| 3,322,124 | * | 5/1967 | Ireland . |
| 3,979,829 | * | 9/1976 | Lemos . |
| 4,247,285 | * | 1/1981 | Roig-Greene ........................ 433/141 |
| 4,337,038 | * | 6/1982 | Saito et al. .............................. 433/32 |
| 4,746,292 | * | 5/1988 | Johnson ................................ 433/141 |
| 4,787,848 | * | 11/1988 | Ross ...................................... 433/165 |
| 5,085,586 | * | 2/1992 | Johnson ................................ 433/224 |
| 5,173,049 | * | 12/1992 | Levy ..................................... 433/215 |
| 5,275,563 | * | 1/1994 | Cohen et al. ......................... 433/224 |
| 5,683,391 | * | 11/1997 | Boyd ...................................... 606/61 |
| 5,879,160 | * | 3/1999 | Ruddle ................................. 433/141 |
| 5,951,286 | | 9/1999 | Rhodes . |

* cited by examiner

Primary Examiner—Ralph A. Lewis
(74) Attorney, Agent, or Firm—Mark M. Friedman

(57) ABSTRACT

A method for the removal of broken threaded dental posts, whose heads have been sheared off, from their receiving bores by exposing the post in its bore together with its extraction, without a need for an additional pulling device. A hollow cylindrical body accommodates precisely the neck of the broken post. The cylinder has saw teeth at its lower rim and an extension of a solid shaft at its upper end by which it is attached to the head of a dental drill. The counter clockwise rotation of the cylinder cuts a circular groove around the post which facilitates its release and withdraw of the post by screwing it out of its bore.

8 Claims, 3 Drawing Sheets

METHOD AND APPARATUS FOR THE WITHDRAWAL OF DENTAL POST

FIELD AND BACKGROUND OF THE INVENTION

The present invention relates to a method and apparatus for the withdrawal of threaded dental posts, which were installed in the teeth and have to be removed. More particularly, the invention relates to a method and apparatus for the combined action of drilling into the material around an installed dental post and its extraction.

Dental posts are used to secure different dental items, such as false teeth, fillings or various reconstructions in the tooth. Typically, their insertion involves drilling a bore in the pulp canal of the tooth, the post is then inserted in the root canal by pushing the post into it while rotating it clockwise using a hand tool inserted into the recesses of the head of the post. The post is then further fastened in its bore by the use of dental cement, which firmly secures the post in place.

A dental post includes a threaded rod and head having a larger diameter than the rod. The diameters of the rod come typically come in six sizes. Only the first four sizes ranging in size from approximately from slightly over 1 mm. to 1.6 mm. tend to break. The rod normally has a right screw thread along it and the head is provided with a cross shaped recess to receive a tool by which the post is rotated into its bore.

Frequently, a root canal treatment has to be renewed, or a reconstruction has to be replaced. In such case, the original post has to be removed from the patient's tooth so that a replacement post can be installed in the original bore. Typically, rotating the post counterclockwise with a screwdriver inserted into the cross shape recess in the post's head does this.

Unfortunately, all too often, the head of the post shears off from the post, making the removal of the buried remains of the post extremely difficult and time-consuming work.

The present practice of peripheral drilling and breaking the dental material around the post until it becomes accessible to a pair of pliers or a like and becomes loose enough to enable its release, is undesirable. Despite the need for a simpler and more effective manner of withdrawal of dental posts from the client tooth, very few procedures have been developed.

In U.S. Pat. No. 5,951,286 to Rhodes, a hollow boring device is described. It comprises of a hollow cylindrical bit with cutting teeth at its lower end with a shaft that fits a conventional dental drill at its upper part. The inner diameter of the hollow drill is larger than the diameter of the dental post so it may be rotated around the post and while leaving it intact. The bit cuts a circular groove around the post to loosen the latter from the surrounding matrix until a pair of pliers can pull it out. The removal of the post according to this patent therefore include two stages; the formation of the groove around the post, and pulling out the post with a pair of pliers. If the groove is too shallow, the post will not be loose enough to enable its being pulled out. On the other hand, if the cut is too deep, it will harm the underlying tissue, making this practice undesirable.

In U.S. Pat. No. 5,075,948 due to Maier, a minimum clearance post extraction tool is described comprising an internally threaded coupling rod having an hexagonal periphery for turning by a common wrench and of a threaded screw which is carried within it which has a diameter that is smaller then the diameter of the dental post and which bores its way into the shaft of the post and anchors itself therein. Upon turning the coupling rod, the post shaft travels upwardly within the coupling rod while drawing the post out of his bore. Neither the post itself turns during this operation nor any other mechanism exists, beside pulling force to facilitate its extraction.

Other patents such as U.S. Pat. No. 4,412,822 to Blechner, U.S. Pat. No. 4,954,081 to Williams, and U.S. Pat. No. 3,650,032 to Kestler describe techniques and apparatuses to remove, or to set, dowel posts in dental sets outside the patient's mouth.

It is therefore desired to have a method for the removal of dental posts, preferably such that in which the release of the dental post will proceed with minimum harm to the dental material and be performed with a minimum use of pulling force.

SUMMARY OF THE INVENTION

The present invention describes a method and provides a tool for the withdrawal of dental posts which were implanted in the patient's tooth whose heads have been sheared off.

The tool enables the simultaneous action of the exposure of the dental post from its surrounding matrix and its withdrawal by gripping the neck of the dental post and turning it counterclockwise. The invention includes a set of such tools. Although a single member of the set is described, it should be understood that the description implies to each member of the set.

The tool includes a hollow cylindrical metallic shaft with cutting saw teeth at its circumference at the bottom rim, which is extended into a solid cylindrical shaft with a notch at its upper end which enable the tool to be attached to low speed dental drill unit, such as the Contra Angle hand piece.

The inner diameter of the hollow cylindrical part has the dimension which matches the outer diameter of the post of the broken dental post. Accordingly the tool has two functions:

1. To expose and to release the dental post by cutting and breaking the cement or dentine around it.

2. To receive the exposed end of the stern of the post into the cylindrical bore where it would be embraced with minimum clearance. As a result, when the tool is rotated, the dental post will spin in its bore whenever the friction between it and the inner walls of the tool will become greater than the cohesive force which secure it in its bore.

Because the spin is counter clockwise, the threaded post will easily screw its way out from its cavity.

It is therefore the object of the invention to provide a method for the effective removal of broken dental posts from the patient's root canal.

It is another object of the invention to provide a tool for the removal of broken dental posts, which will eliminate the interference of any other drilling, breaking or pulling device.

It is another object of the invention to provide a tool with minimum clearance for the removal of broken dental posts from the patient oral cavity and which requires minimum space to operate.

It is another object of the invention to provide a tool for the removal of dental posts whose use will minimize the risk of damaging the structural integrity of the tooth.

It is another object of the invention to provide a tool with minimum clearance for the removal of broken dental posts from the patient oral cavity, which requires minimal removal of the tooth's material.

It is another object of the invention to provide a tool with minimum clearance for the removal of broken dental posts from the patient oral cavity, which requires the use of minimum pulling force.

Other objects of the invention will become apparent upon reading the following description taken in conjunction with the accompanying drawings.

DESCRIPTION OF THE PREFERRED EMBODIMENTS

The preferred embodiments herein are not intended to be exhaustive and to limit in any way the scope of the invention, rather they are used as examples for the clarification of the invention and for the enabling of other skilled in the art to utilize its teaching. It should further be understood that what is meant by the term tool includes a set of tools whose members are identical except for their diameters.

Figure 1:
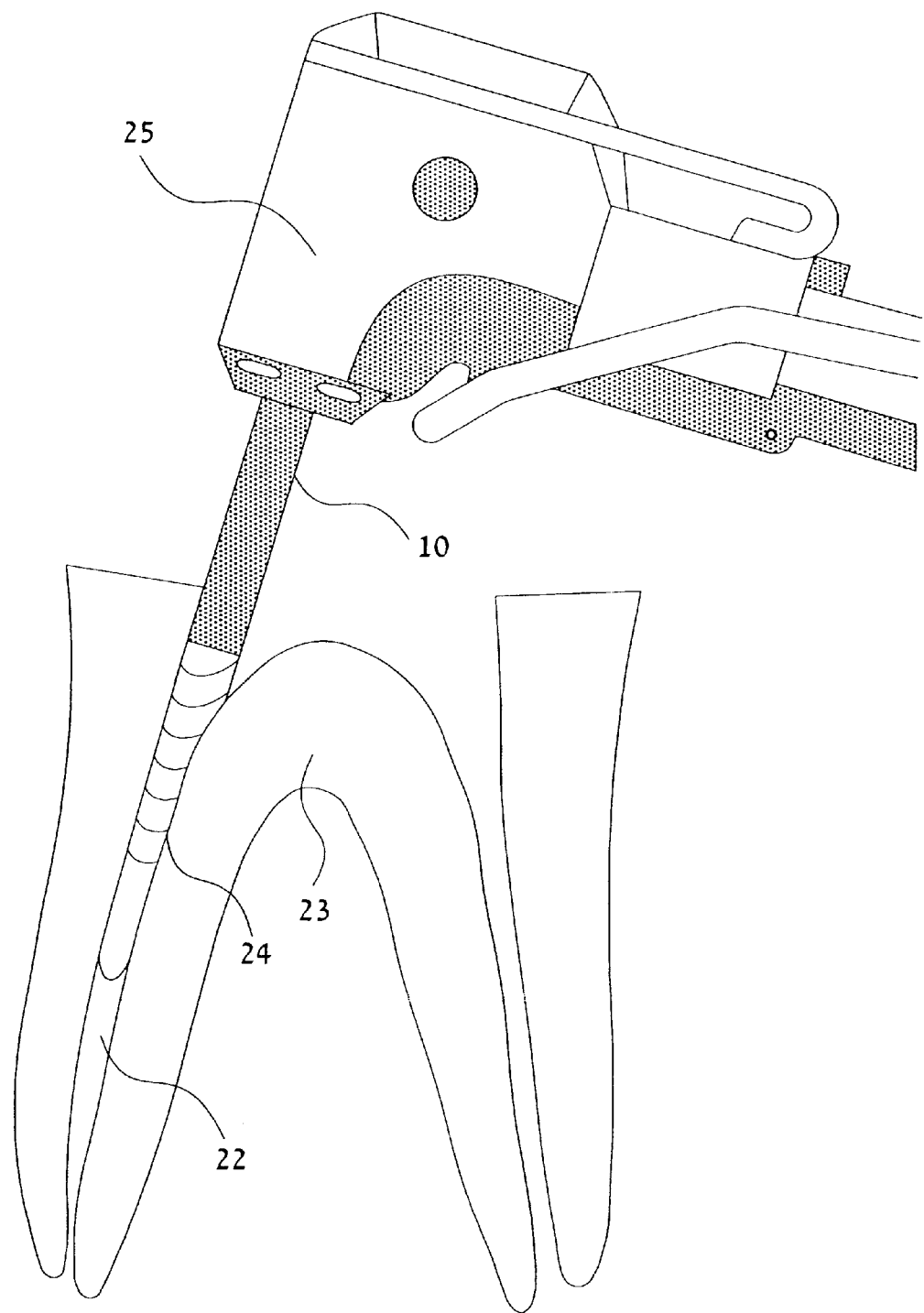
FIG. 1 is a profile view of the dental post removal tool according to the present invention.
Figure 2:
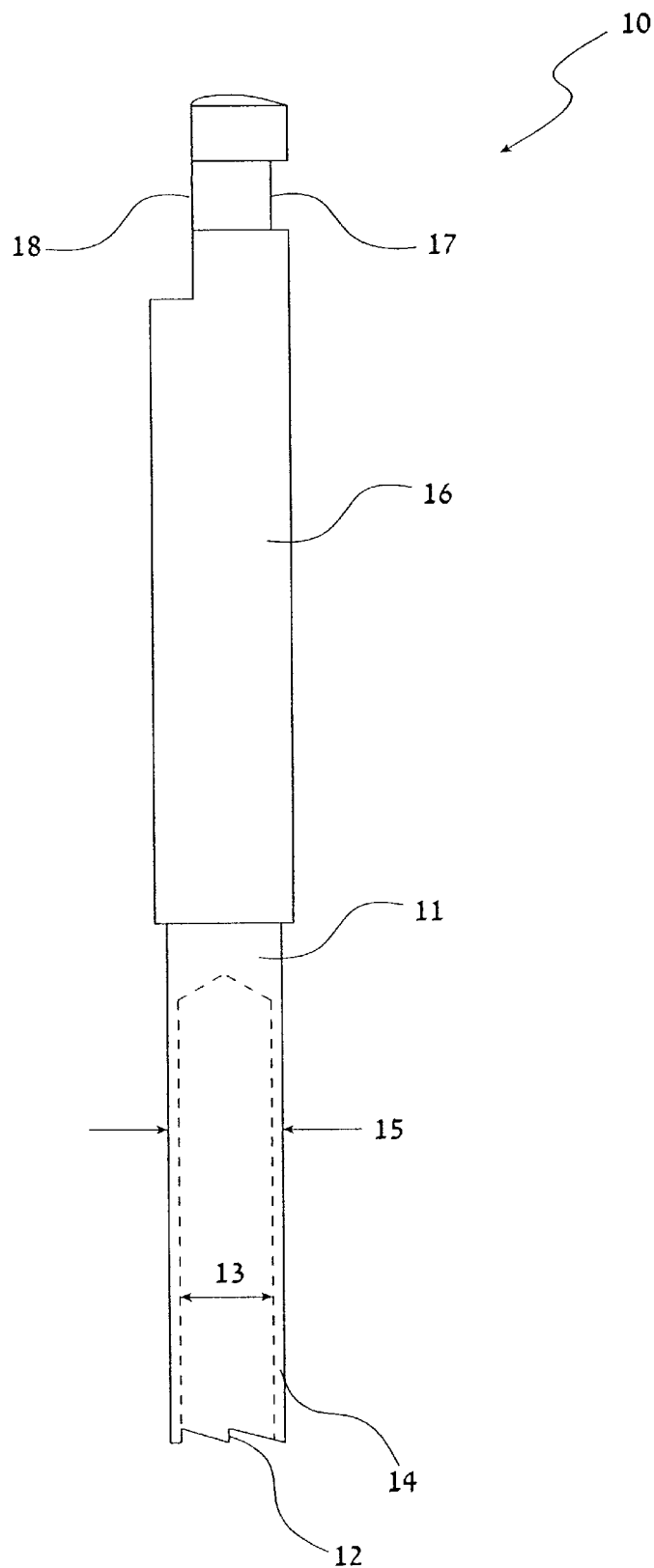
FIG. 2 is a longitudinal sectional view of the dental post removal tool according to the present invention.
Figure 3:
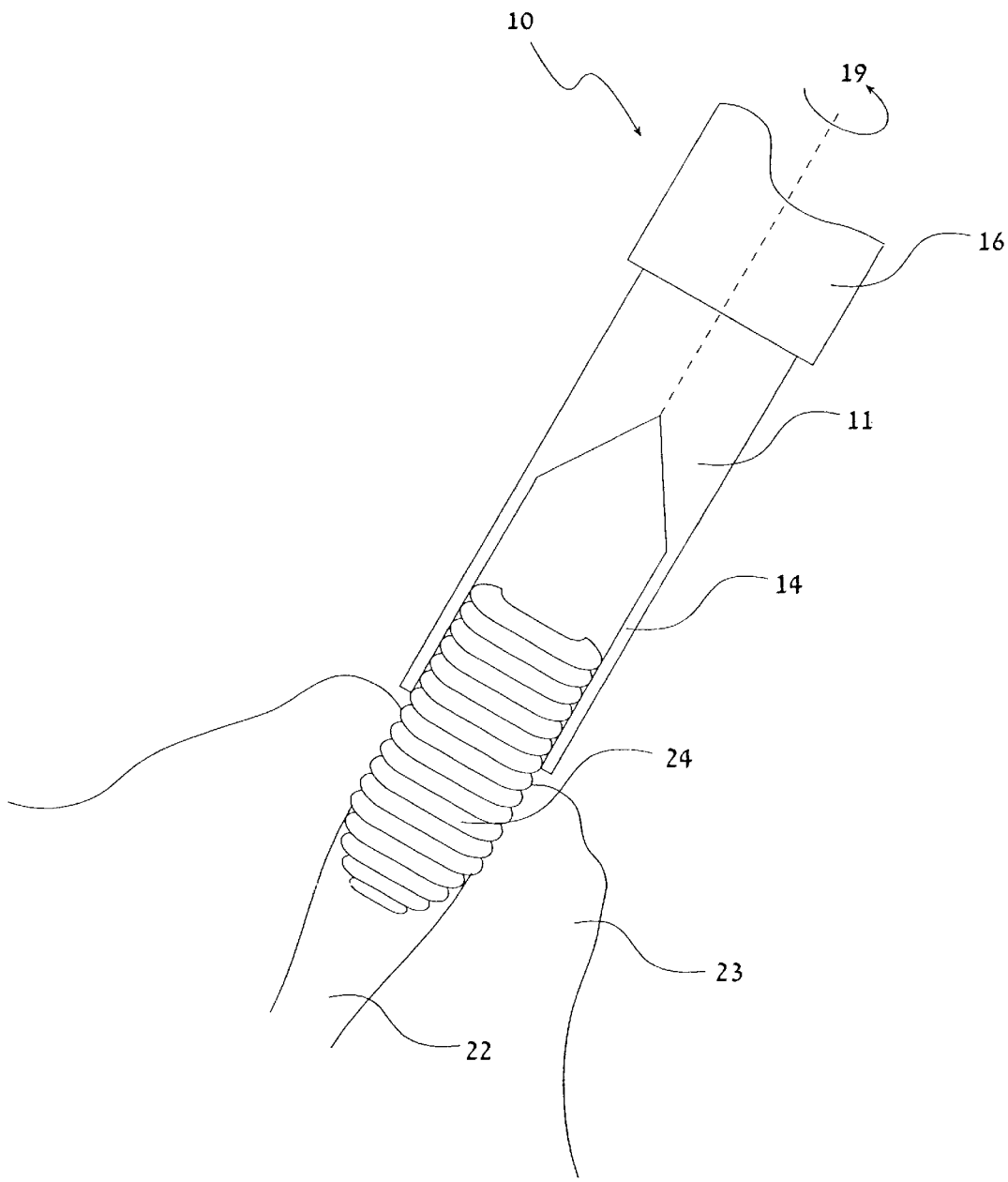
FIG. 3 is an enlarged sectional view of the relative position of the tool and the broken dental post in its cavity according to the present invention.

Referring now to FIGS. 1, 2, and 3, tool 10 comprises of a body having cylindrical outer wall machined from a single piece of high speed stainless steel or other metal which is compatible with dental or surgical treatment. The tool 10 includes an active part 11, which comprises a hollow cylinder. The lower circumference of the cylinder 11 is decorated with saw teeth 12, designed as to perform a cut when rotated counter clockwise. The bore of the hollow cylinder is about 9 mm. long and its wall thickness 14 is typically 0.2 mm.

The upper part of the tool 11 comprises a solid shaft 16 which is about 12 mm. long and which fits any conventional head of a dental drill 25 and which is secured to the drill head by a circular notch 17 and a flat surface 18.

After clinical and X- ray examination, the dentist comprehends the size of the broken post 24 and selects from the set the tool 10 with the appropriate inner diameter 13, and outer diameter 15, for example:

(A) Inner diameter—1.19 mm., outer diameter—1.59 mm. to match dental post No. 1, which has an outer diameter of approximately 1.04 mm.

(B) Inner diameter—1.30 mm., outer diameter—1.70 mm. to match dental post No. 2, which has an outer diameter of approximately 1.15 mm.

(C) Inner diameter—1.47 mm., outer diameter—1.87 mm. to match dental post No. 3, which has an outer diameter of approximately 1.32 mm.

(D) Inner diameter—1.63 mm., outer diameter—2.03 mm. to match dental post No. 4, which has an outer diameter of approximately 1.48 mm.

It should be understood that neither the dimensions of the bore nor its wall thickness limit the invention to these dimensions, which merely represent the tool, which fits the most abounded and conventional dental posts, currently in use.

The appropriate tool 10 is attached to the head of a low speed dental drill 25 equipped with a speed reducer and fitted over the remaining portion of the dental post 24, which resides in its root canal 22 of the tooth 23. The tool 10 is then rotated at 300–400 rpm in a counter clockwise direction 19. This is usually sufficient to engage the broken post and withdraw it in few seconds.

Whenever the post is not extracted on the first attempt, a larger tool is used which cuts deeper around the post while leaving it intact. The original procedure is then repeated.

The preferred embodiments herein are not intended to be exhaustive and to limit in any way the scope of the invention, rather they are used as examples for the clarification of the invention and for the enabling of other skilled in the art to utilize its teaching.

What is claimed is:

1. A method for the removal of an embedded broken dental post, said post comprises a stem and a head, said head having been sheared off, comprising the steps of:

encircling said exposed stem of said broken post with a hollow cylinder, wherein the inner diameter of said hollow cylinder matches with the outer diameter of said stem so as to frictionally engage said stem;

cutting a groove around said stem of said post with said hollow cylinder, said cylinder having cutting teeth at the circumference of its lower rim in order to expose it from the surrounding cement or dental material;

rotating said hollow cylinder in a counterclockwise direction, whereby said stem rotates together with said hollow cylinder due to friction and screws its way out from its bore.

2. A method for the removal of an embedded broken dental post according to claim 1, wherein said cylinder is metallic and is coupled to a conventional dental drill.

3. A method for the removal of an embedded broken dental post according to claim 1, wherein said post has a right hand screw threading along its stem.

4. A method for the removal of an embedded broken dental post according to claim 1, wherein said inner diameter of said hollow cylinder fits said dental post which has a stem diameter selected from the group consisting of one the following: 1.04 mm., 1.15 mm., 1.32 mm., and 1.48 mm.

5. A combination of a broken stem of a dental post and a apparatus for the removal of the broken stem portion from a receiving bore within a tooth, the combination comprising:

an embedded broken stem portion of a dental post from which a head portion has been sheared off;

a cylindrical body having a hollow cylindrical interior cavity, the inner diameter thereof dimensioned to frictionally grip said stem portion when placed there over; and a drill head, said cylindrical body coupler to said drill head;

whereby when said drill head is rotated, said cylinder is rotated to rotate said frictionally gripped post such that said stem portion is withdrawn from the receiving bore in the tooth.

6. A combination according to claim 5, wherein one end of said cylindrical body is decorated with cutting teeth providing a cutting edge.

7. A combination according to claim 5, further including a shaft coupled between said drill head and said cylindrical body.

8. A combination according to claim 5, wherein said inner diameter of said hollow cylinder first said stem portion which has a diameter selected from the group consisting of one the following: 1.04 mm., 1.15 mm., 1.32 mm., and 1.48 mm.

* * * * *

UNITED STATES PATENT AND TRADEMARK OFFICE
CERTIFICATE OF CORRECTION

PATENT NO. : 6,280,197 B1  
DATED : August 28, 2001  
INVENTOR(S) : Doron Benado Page 1 of 1

It is certified that error appears in the above-identified patent and that said Letters Patent is hereby corrected as shown below:

<u>Column 4,</u>  
Line 40, insert the word "portion" between 6$^{th}$ word: "stem" and continuation of line "of a dental"

Signed and Sealed this

Second Day of April, 2002

Attest:

JAMES E. ROGAN  
*Director of the United States Patent and Trademark Office*

*Attesting Officer*